United States Patent [19]

Givens

[11] Patent Number: 4,907,448
[45] Date of Patent: Mar. 13, 1990

[54] APPARATUS FOR MEASURING RESISTIVITY OF POROUS ROCK

[75] Inventor: Wyatt W. Givens, Dallas, Tex.

[73] Assignee: Mobil Oil Corporation, New York, N.Y.

[21] Appl. No.: 309,745

[22] Filed: Feb. 13, 1989

[51] Int. Cl.[4] .............................................. E21B 49/02
[52] U.S. Cl. ..................................... 73/153; 324/376
[58] Field of Search ............... 324/64, 65 P, 376, 444, 324/449, 450; 73/151, 153

[56] References Cited

U.S. PATENT DOCUMENTS

| | | | |
|---|---|---|---|
| 2,613,250 | 10/1952 | Bilhartz et al. | 324/376 |
| 2,745,057 | 5/1956 | Dotson | 324/376 |
| 2,821,680 | 1/1958 | Slusser et al. | 324/376 |
| 3,839,899 | 10/1974 | McMillen | 73/38 |
| 4,379,407 | 4/1983 | Masse et al. | 73/579 |
| 4,380,930 | 4/1983 | Podhrasky et al. | 73/594 |
| 4,467,642 | 8/1984 | Givens | 73/152 |
| 4,546,318 | 10/1985 | Bowden | 324/376 |
| 4,686,477 | 8/1987 | Givens et al. | 324/346 |
| 4,688,238 | 8/1987 | Sprunt et al. | 378/4 |

OTHER PUBLICATIONS

"The Electrical Resistivity Log as an Aid in Determining Some Reservoir Characteristics", G. E. Archie, Trans. AIME, vol. 46, pp. 54–62, 1942.

Primary Examiner—Hezron E. Williams
Assistant Examiner—Kevin D. O'Shea
Attorney, Agent, or Firm—Alexander J. McKillop; Charles J. Speciale; George W. Hager, Jr.

[57] ABSTRACT

Apparatus is provided for measuring resistivities along the length of a core sample of a porous rock under confining pressure and varying fluid saturations. A confining pressure sleeve surrounds the core sample. Resistivities are measured along the length of the core sample by a plurality of electrodes extending through such sleeve as fluid saturations vary.

8 Claims, 2 Drawing Sheets

APPARATUS FOR MEASURING RESISTIVITY OF POROUS ROCK

BACKGROUND OF THE INVENTION

In the drilling of wells, such as oil or gas wells, cores are taken of the earth formation through which the wells are drilled and various characteristics of the cores, or core samples, are determined for the purpose of establishing different fluids in the formation, estimating the quantity of each fluid in the formation, the ease of flow through the formation, etc. Such core samples are also taken from producing reservoirs and characteristics of the core samples are determined for the purpose of estimating particular fluid quantities, predicting production rates, etc. Among the characteristics of core samples commonly determined is the formation resistivity factor involving the measurement of the electrical resistivity of the core samples. Such resistivity factor is set forth in "The Electrical Resistivity Log as an Aid in Determining Some Reservoir Characteristics", Trans. AIME, Vol. 46, pp. 54–62, 1942, by G. E. Archie.

Standard practice is to measure porous rock resistivities for a number of partial water saturations and to plot a resistivity index I, determined from the ratio of the measured resistivity of the rock at a partial water saturation to the measured resistivity at complete water saturation, against the water saturation at which the resistivity measurements were made. From this plot the rate of change of rock resistivity with varying water saturation, defined by Archie as a saturation exponent, is determined. However, such a plot assumes that all rock pores are desaturated equally and all resistivities for partial water saturation are measured under an equilibrium distribution of a conducting and a nonconducting fluid, e.g., water (brine) and oil. These fluids must be immiscible throughout the rock sample. If an equilibrium distribution of fluids is not reached throughout the rock sample at each partial water saturation, then the measured resistivities will not be correct and any saturation exponent determined from such resistivities will not be characteristic of the rock.

It is therefore a specific objective of the present invention to provide apparatus for measuring rock resistivities under varying water saturations which can be positively identified as being in a state of fluid distribution equilibrium at the time the resistivity measurements are made.

SUMMARY OF THE INVENTION

In accordance with the present invention, apparatus is provided for measuring resistivity of a core sample of a porous rock under confining pressure and varying water saturations.

More particularly, a sleeve is provided into which a core sample of a porous rock saturated with a first fluid is inserted. A fluid inlet is positioned in one end of the sleeve and a fluid outlet is positioned in the opposite end of the sleeve. A second fluid which is immiscible with and of opposite electrical conductance with the first fluid is injected under pressure into a first end of the core sample for displacing the first fluid from a second end of the core sample. A porous member is positioned adjacent such second end of the core sample through which the first fluid being discharged from the core sample passes into the fluid outlet of the sleeve. This porous member while being permeable to the first fluid, is impermeable to the second fluid. A plurality of voltage electrodes extend through the sleeve and make contact with the core sample at a plurality of spaced-apart positions along the length of the core sample. A confining pressure is applied to the core sample through the sleeve. The fluid inlet and outlet serve as additional electrodes for passing a current through the core sample. As the current flows through the core sample, the voltage electrodes continuously measure voltages at the plurality of spaced-apart positions along the core sample as the fluid saturation condition changes within the core sample. The resistivity of the core sample under the varying fluid saturations is determined from these measured voltages and current.

In a further aspect, the voltage electrodes contact the core sample at a plurality of circumferential positions about the surface of the core sample.

In a yet further aspect the voltage electrodes are in the form of rings surrounding the core sample such that under confining pressure the electrodes and the sleeve are pressed against the core sample to prevent any conductance path between the electrodes exterior of the rock pores of the core sample. Such electrodes may be molded into the inner surface of the sleeve and may extend outward from such inner surface by a few thousandths of an inch.

BRIEF DESCRIPTIONS OF THE DRAWINGS

DESCRIPTION OF THE PREFERRED EMBODIMENT

Figure 1:
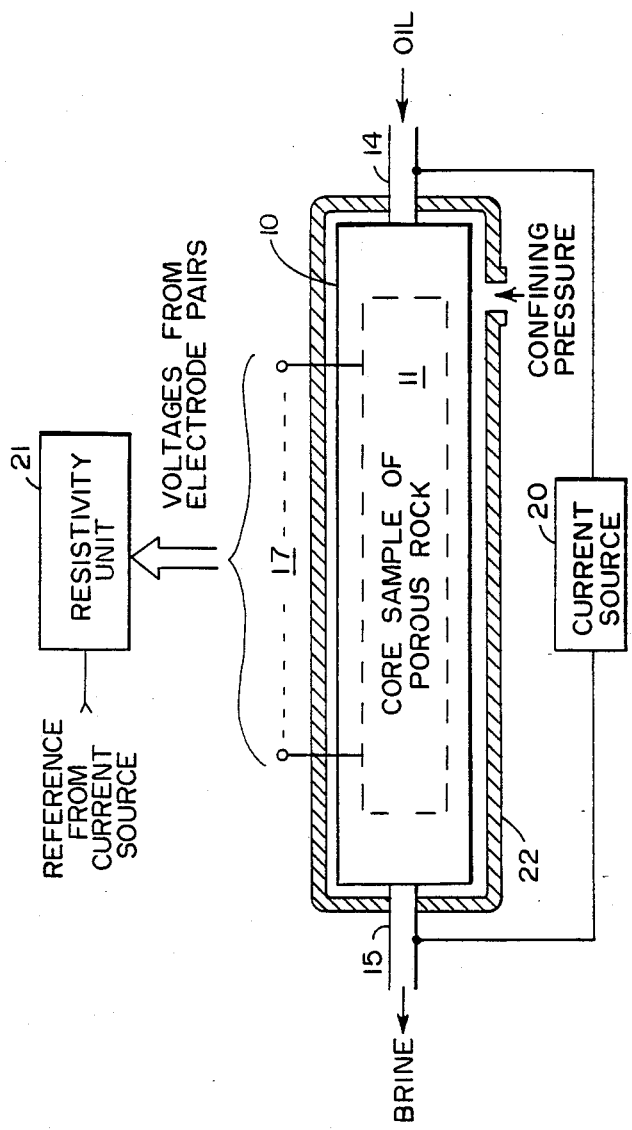
FIGS. 1 and 2 illustrate apparatus of the present invention in which a core sample may be placed for the carrying out of resistivity measurements along the length of the core sample for varying fluid saturations.
Figure 2:
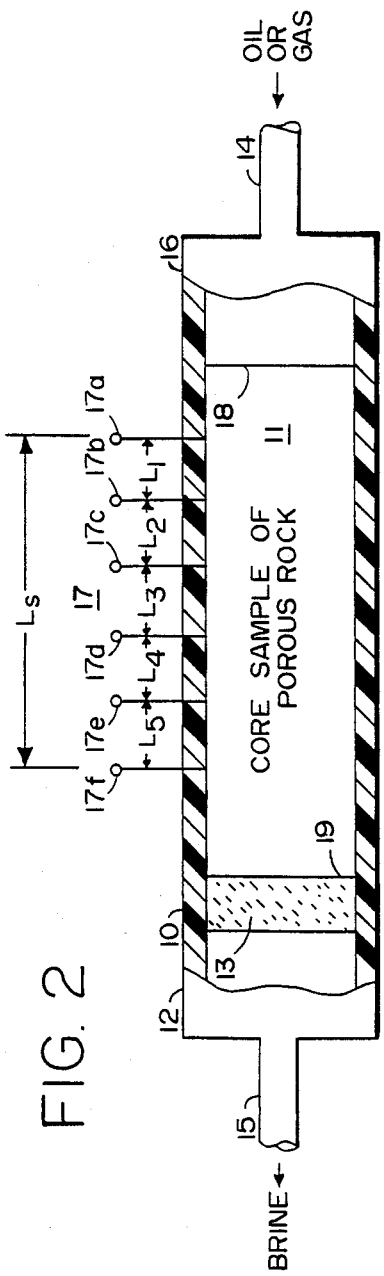

The apparatus of the present invention for making resistivity measurements of porous rock at varying fluid saturations is shown in FIGS. 1 and 2. A pressure sleeve 10, preferably natural or synthetic rubber, is in the form of a cylinder surrounding a core sample 11 of a porous rock to be measured for resistivity at a plurality of fluid saturations. Positioned between the core sample 11 and end 12 of the pressure sleeve 10 as shown in FIG. 2 is a porous number 13 which is permeable to a first fluid saturating the core sample but is impermeable to a second fluid used to displace the first fluid from a core sample. The second or displacing fluid is immiscible with the first fluid saturating the core sample and is of opposite electrical conductivity. The first saturation fluid is the wetting fluid for the porous member 13, which by way of example, may be a ceramic plate or a membrane. Sleeve 10 is placed inside a suitable pressure vessel 22 that can be pressurized up to several thousand pounds per square inch. Typical of such pressure vessels are those described in U.S. Pat. Nos. 3,839,899 to McMillan; 4,688,238 to Sprunt et al; and 4,379,407 to Masse et al. Through such a pressure vessel 22 a pressure is applied to the sleeve 10 and hence to the porous rock 11. A fluid inlet 14 and a fluid outlet 15 feed into the ends 16 and 12 respectively of the sleeve 10. Both inlet 14 and outlet 15 also serve as current conducting electrodes for passing current from a source 20 through the porous rock 11 when it contains a sufficient amount of electrically conducting fluid. A plurality of voltage electrodes 17 penetrate sleeve 10 and make contact with the porous rock at a plurality of spaced locations along the length of the porous rock.

By way of example, a core sample of a porous rock 11 is initially fully saturated with an electrically conducting fluid such as salt water, preferably brine, and placed within sleeve 10 under confining pressure. A current is passed through the porous rock at this initial saturation condition and the voltage $V_s$ along the length $L_s$ of the porous rock is measured between electrodes 17a and 17f. As noted above, the inlet 14 and outlet 15 function as current electrodes conducting current into and out of porous rock while the brine acts as the conducting medium within the porous rock and the porous member 13. Such voltage measurement, as well as later voltage measurements described below, may be carried out in accordance with the teachings of U.S. Pat. No. 4,467,642 to Givens; U.S. Pat. No. 4,546,318 to Bowden, and U.S. Pat. No. 4,686,477 to Givens et al., the teachings of which are incorporated herein by reference. From this voltage $V_s$ the resistance $r_s$ of the porous rock along the length $L_s$ is determined using Ohm's Law by the resistance section of the resistivity unit 21. The resistivity unit 21 calculates the resistivity $R_s$ using the resistance $r_s$, the length $L_s$ and the cross-sectional area of the core $A_c$. (Note: $R_s = r_s A_c / L_s$) A non-conducting fluid-displacing liquid such as a hydrocarbon, preferably oil, is then forced through inlet 14 and into end 18 of porous rock 11 under a pressure $P_1$. It takes a finite amount of time for the oil to pass through the porous rock displacing brine through a brine permeable and oil impermeable porous member 13 and hence through outlet 15. Initially only fingers of oil travel through the porous rock 11 from end 18 toward end 19. This can be thought of as an oil front. There is therefore initially a definite disequilibrium in the distribution of the brine and oil throughout the porous rock. After an interval of time under pressure $P_1$, such fluid distribution reaches a state of equilibrium throughout the porous rock. The interval of time depends on a number of rock and fluid properties, such as permeability of the rock to brine and oil, length of the core sample of the porous rock, viscosity of the oil, and pore geometry among others.

It is a specific feature of the present invention to provide apparatus for determining when this state of equilibrium has been reached under injection pressure $P_1$ so that a resistivity measurement can be made on porous rock for the saturation condition existing at that time. This determination is made by measuring the voltage between each of the pairs of adjacent electrodes 17 and comparing these measured voltages to identify when the fluid distribution of the brine and oil is no longer changing following the oil injection at such pressure $P_1$. More particularly, the electrodes 17 are spaced-apart by the distances $L_1$-$L_5$ along the length $L_s$ of the porous rock, thereby dividing the porous rock into a plurality of subsections having the lengths $L_1$-$L_5$. The voltage across each of these subsection lengths, that is $V_1$-$V_5$, is measured and resistivities $R_1$-$R_5$ determined by resistivity unit 21 from Ohm's Law, the length $L_1$-$L_5$ and the cross-sectional area of the core $A_c$ in response to the passage of a current through the porous rock.

By comparing these resistivity determinations, the occurrence of fluid saturation equilibrium at total water saturation and at an injection pressure $P_1$ can be identified. This comparison is carried out in one of two ways depending upon whether the porous rock is homogenous or heterogenous. Measurements are first made with the rock fully brine saturated, before an oil is injected, to obtain resistivity $R_{0S}$ determinations along the rock (e.g., $R_{01}$, $R_{02}$, $R_{03}$, etc). If these resistivities are all equal, the rock is homogenous. If there are resistivity gradients indicated by the ratios $R_{01}/R_{02}$, $R_{02}/R_{03}$, etc. the rock is heterogenous.

Firstly, this comparison will be described for a homogenous porous rock and then for a heterogenous porous rock. As oil enters a homogenous porous rock through inlet 14 it passes the plane of electrode 17a through the porous rock, enters the subsection of the porous rock between electrodes 17a and 17b and changes the fluid distribution of the brine and oil between electrodes 17a and 17b. At this point in time the voltage measurement $V_1$ across subsection length $L_1$ will be greater than voltage measurements $V_2$-$V_5$ across subsection lengths $L_2$-$L_5$, hence the resistivity $R_1$ will be greater than resistivities $R_2$-$R_5$. It doesn't matter whether the lengths $L_1$-$L_5$ of the subsections are equal or not since any variations in such lengths only affects the resistances of the subsections and not the resistivities for a uniform and homogenous porous rock.

As the oil progresses through the porous rock toward the porous member 13 at the opposite end 19 of the porous rock, the fluid saturations between each additional pair of electrodes 17 progressively change accordingly to the oil and brine distribution within the subsections between the electrodes, hence the corresponding subsection resistivities progressively change also. After some interval of time, the oil will reach the porous member 13 under injection pressure $P_1$. As long as injection pressure $P_1$ is less than a critical breakthrough pressure of the porous member 13 the oil will not penetrate porous member 13. At this point the oil fingers established throughout the porous rock begin to enlarge with such enlargement traveling in the reverse direction from the end 19 adjacent the porous member 13 toward the end 18 adjacent the injection inlet 14. In time fluid saturation equilibrium is established and the oil fingers swell essentially equally throughout the length of the porous rock until all the brine that can be displaced from porous rock at injection pressure $P_1$ is displaced from end 19 through porous member 13. For the homogenous porous rock there is now resistivity equilibrium, that is, there are no resistivity gradients along the length of the porous rock since all resistivities $R_1$-$R_5$ are equal. Upon identification of fluid saturation equilibrium at injection pressure $P_1$ from a comparison of $R_1$-$R_5$, the foregoing described procedure is repeated for a plurality of incrementally increased oil injection pressures to provide a plurality of resistivity determinations $R_s$ at fluid saturation equilibrium for a corresponding plurality of partial water saturations within the porous rock such that resistivity indexes I can be plotted against water saturation to obtain the Archie saturation exponent n.

Having now described the comparison of determined resistivities for a homogenous porous rock to identify fluid saturation equilibrium, a comparison of the same resistivities for a heterogenous porous rock will now be described. In a heterogenous porous rock, as contrasted with a homogenous porous rock, certain rock characteristics, such as porosity and pore size among others, vary through the length of the porous rock. Resistivity determinations as described above at various oil injec- tion pressures, and hence various water saturations, will not be equal between the porous rock subsections at a fluid saturation equilibrium for the heterogenous porous rock. Resistivities of some subsections might be equal, but others will not. Consequently, a comparison of such resistivities on the basis of resistivity gradients will not identify fluid saturation equilibrium as in the case of the homogenous porous rock. A different type of comparison is required. Such a comparison involves determining the ratios of resistivities between pairs of electrodes 17 and identifying fluid saturation equilibrium when each of such ratios becomes a constant. This can best be seen by again referring to the fluid distribution existing in the heterogenous porous rock as described above for the homogenous porous rock at total water saturation and at an initial oil injection pressure $P_1$. As the oil fingers through the porous rock the resistivities across subsections of lengths $L_1$-$L_5$ will not be equal. Consequently the ratios K of pairs of such resistivities will likewise not be equal. Further, the value of only such ratio K will be changing until such time as fluid saturation equilibrium is established in both the subsections of the porous rock for which the ratio K has been determined. At such point of fluid saturation equilibrium between a given pair of subsections the ratio K will thereafter remain constant. Accordingly, fluid saturation equilibrium of the porous rock across the entire length $L_s$ can be identified when the ratios of resistivities between each pair of subsections of the porous rock all become constant, but not equal.

Figure 3:
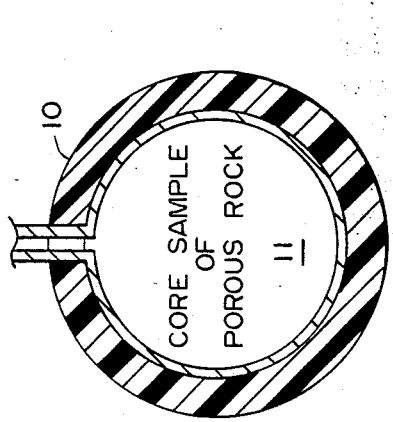
FIG. 3 is a cross sectional view taken through the core sample in the apparatus of FIG. 2 at the position of one of the resistivity measuring electrodes showing one embodiment for configuration of such electrodes about the core sample.

Having now described the apparatus shown in FIGS. 1 and 2 and the use of such apparatus in carrying out resistivity measurements on core samples of porous rock under conditions of the above described example of oil displacing brine within the core sample, a preferred embodiment for the voltage electrodes 17 of such FIGS. will now be described in accordance with the present invention. Referring to FIG. 3, there is shown in cross section one of the electrodes 17 extending through the sleeve 10 and contacting the core sample 11. Electrode 17 is configured to contact the core sample 11 at a plurality of circumferential positions. Preferably electrode 17 is in the form of a ring which almost completely surrounds such core sample. A small gap, such as about 1/16 to ⅛ inch, is maintained between the ends of electrode 17 to provide for a good seal and to allow for compression of the electrode about the core sample. Although electrode 17 is shown in FIG. 3 as resting along the inner surface of sleeve 10, it may in the alternative be molded into the inner surface of sleeve 10 such that it protrudes only a few thousandths of an inch from such inner surface. The sleeve 10 may be of rubber which is molded and curved at vulcanizing temperature about the electrode 17.

As a confining pressure is applied to sleeve 10, the electrode 17 is pressed tightly about the circumference of the core sample. Between each of the pairs of electrodes, the sleeve 10 is also pressed tightly about the circumference of the core sample. With such configuration there is no surface layer of brine, or water, that would provide a conductance path exterior of the rock pores of the core sample 11.

A preferred material for electrodes 17 is silver as it can be readily treated to have a silver-chloride layer which possesses good properties for such voltage measurements. Electrodes that corrode or oxidize are to be avoided. Since prior practice is to make a resistivity measurement across the length of the porous rock between a single pair of voltage electrodes in a few hours after each incremental injection pressure change, it can clearly be seen that any value of the Archie saturation exponent n derived from such resistivities will not be representative of the actual or true saturation exponent for that particular porous rock. By utilizing the apparatus of the present invention in carrying out resistivity measurements at a plurality of spaced positions along the porous rock, the point in time when fluid saturation equilibrium does occur is identified precisely so that a resistivity measurement across the length of the porous rock can be timely made and used to derive the true value of the saturation exponent for the particular porous rock being examined, whether it be homogenous or heterogenous.

The apparatus of the present invention for use in measuring resistivity of porous rock has been described in conjunction with the above example of a core sample saturated with a conductive fluid, such as a brine, and with a non-conducting, displacing fluid, such as oil. Such a fluid displacement process can be referred to as a drainage cycle. Such resistivity measurements can also be carried out with the apparatus of the present invention on a core sample saturated with the non-conducting fluid, or oil, and displacing such oil with the conducting fluid, or brine. Such a fluid displacement process can be referred to as an imbibition cycle. Consequently, the apparatus of the present invention may be used for measuring the equilibrium distribution of two immiscible and oppositely conducting fluids for either a drainage or an imbibition cycle, or any repetitive sequencing thereof.

While the foregoing has described a preferred embodiment of apparatus for use in carrying out the method of the present invention, it is to be understood that various modifications or changes may be made without departing from the spirit and scope of the present invention as set forth in the appended claims.

I claim:

1. Apparatus for measuring resistivity at a plurality of positions along the surface of a core sample of a porous rock under confining pressure and varying water saturations, comprising:

(a) a sleeve containing a core sample of a porous rock saturated with a first fluid,
   (b) a fluid inlet positioned in a first end of said sleeve through which a second fluid is injected under pressure into a first end of said core sample for displacing said first fluid from a second end of said core sample, said second fluid being immiscible with said first fluid and of opposite electrical conductance,
   (c) a porous member positioned adjacent a second end of said core sample within said sleeve, and which is permeable to said first fluid and impermeable to said second fluid,
   (d) a fluid outlet positioned in a second end of said sleeve through which said first fluid is discharged from said sleeve after having been displaced from the second end of said core sample through said porous member,
   (e) a plurality of electrodes extending through said sleeve and making contact with said core sample at a plurality of spaced apart positions along the length of the core sample,
   (f) means for passing a current through said core sample, (g) means for applying a confining pressure through said sleeve to said core sample, and (h) means connected to said electrodes for measuring resistivities between adjacent pairs of said electrodes in response to the flow of said current through said core sample at said confining pressure as said second fluid displaces said first fluid from said core sample.

2. The apparatus of claim 1 wherein said electrodes contact said core sample at a plurality of circumferential positions about the surface of said core sample.

3. The apparatus of claim 2 wherein said electrodes are in the form of rings surrounding said core sample such that under confining pressure on said sleeve said electrodes and said sleeve are pressed against said core sample to prevent any conductance path between said electrodes exterior of the rock pores of said core sample.

4. The apparatus of claim 3 wherein said electrodes are molded into an inner surface of said sleeve.

5. The apparatus of claim 4 wherein said sleeve comprises rubber and said electrodes are vulcanized into said rubber sleeve.

6. The apparatus of claim 4 wherein said electrodes extend outward from the inner surface of said sleeve a few thousandths of an inch.

7. The apparatus of claim 1 wherein said porous member is water permeable and hydrocarbon impermeable.

8. The apparatus of claim 1 wherein said porous member is hydrocarbon permeable and water impermeable.

* * * * *